United States Patent [19]
Harada et al.

[11] Patent Number: 5,258,014
[45] Date of Patent: Nov. 2, 1993

[54] SURGICAL SUTURE AND PROCESS FOR PRODUCING SAME

[75] Inventors: Akira Harada; Hiroshi Mano, both of Osaka, Japan

[73] Assignee: Sumitomo Electric Industries Ltd., Osaka, Japan

[21] Appl. No.: 680,971

[22] Filed: Apr. 5, 1991

[30] Foreign Application Priority Data

Apr. 6, 1990 [JP] Japan .................................... 2-92803

[51] Int. Cl.⁵ ............................................. A61B 17/00
[52] U.S. Cl. ................................... 606/228; 264/127; 264/288.8
[58] Field of Search ............... 606/231, 228, 229, 230; 264/176.1, 40.7, 210.7, 210.8, 211.12, 211.14, 127, 174, 209.5, 209.8, 288.4, 288.8

[56] References Cited

U.S. PATENT DOCUMENTS

| | | | |
|---|---|---|---|
| 2,776,465 | 1/1957 | Smith | 264/127 |
| 4,034,763 | 7/1977 | Frazier | 128/335.5 |
| 4,104,394 | 8/1978 | Okita | 264/127 |
| 4,208,745 | 6/1980 | Okita | 3/1.4 |
| 4,250,138 | 2/1981 | Okita | 264/127 |
| 4,280,500 | 7/1981 | Ono | 128/348 |
| 4,482,516 | 11/1984 | Bowman et al. | 264/288.8 |
| 4,496,045 | 1/1985 | Ferguson et al. | 206/63.3 |
| 4,496,507 | 1/1985 | Okita et al. | 264/127 |
| 4,596,837 | 6/1986 | Yamamoto et al. | 521/145 |
| 4,623,502 | 11/1986 | Cohen | 264/176.1 |
| 4,800,048 | 1/1989 | Bloomfield et al. | 264/209.5 |
| 4,826,949 | 5/1989 | Stanko | 264/176.1 |

FOREIGN PATENT DOCUMENTS

| | | |
|---|---|---|
| 0069577 | 1/1983 | European Pat. Off. |
| 0352749 | 1/1990 | European Pat. Off. |
| 8400717 | 3/1984 | PCT Int'l Appl. |

*Primary Examiner*—Stephen C. Pellegrino
*Assistant Examiner*—Gary Jackson
*Attorney, Agent, or Firm*—Sughrue, Mion, Zinn, Macpeak & Seas

[57] ABSTRACT

A surgical suture and a process for producing the same are disclosed, which surgical suture comprising a porous body of polytetrafluoroethylene having an outer circumference that is substantially free of pores, with only the interior being made porous.

3 Claims, 4 Drawing Sheets

FIG. 4a
PRIOR ART
FIG. 4b
PRIOR ART
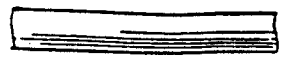
FIG. 5a
PRIOR ART
FIG. 5b
PRIOR ART
FIG. 6a
PRIOR ART
FIG. 6b
PRIOR ART

1 …

SURGICAL SUTURE AND PROCESS FOR PRODUCING SAME

FIELD OF THE INVENTION

The present invention relates to a surgical suture and a process for producing the same.

BACKGROUND OF THE INVENTION

Currently used surgical sutures are available in various types made from both natural and artificial materials. In terms of shape, surgical sutures are classified as monofilaments (FIG. 4), braided multifilaments (FIG. 5) and twisted multifilaments (FIG. 6).

Surgical sutures made of synthetic polytetrafluoroethylene (PTFE) have recently been developed with a view to taking advantage of the low tissue interaction of PTFE and an example of such sutures is described in JP-B-61-34346. (The term "JP-B" as used herein means an examined Japanese patent publication.) Disclosed in JP-B-61-34346 is a surgical suture made of twisted or braided PTFE tapes or filaments that have a microstructure in which a number of fibrils oriented in a longitudinal direction are bound with small nodes at selected sites.

Commercially available porous PTFE sutures, on the other hand, have low tensile strength values that are smaller than those specified by the standards for plastic sutures in Notification No. 444 of the Ministry of Public Welfare of Japan (Extra Circular of Dec. 28, 1970). Examples of the diameters and tensile strength values of the commercial products and an extract of the Notification No. 444 are shown in Table 1 below. Further, these commercial sutures have fine asperities on the surface as shown in FIG. 7.

TABLE 1

| Commercial product | | Standards in Notification No. 444 | |
|---|---|---|---|
| Diameter (mm) | Tensile strength (kg) | Diameter (mm) | Tensile strength (kg) |
| 0.221 | 1.10 | 0.203–0.245 | ≧1.13 |
| 0.163 | 0.62 | 0.152–0.203 | ≧0.68 |
| 0.132 | 0.43 | 0.102–0.152 | ≧0.45 |

The suture shown in JP-B-61-34346 is composed of twisted tapes or filaments, and thus it has the following two major problems because of twisting: (1) it has low porosity and elasticity, and (2) the surface asperities reduce the slipping property of the suture and increase the chance of adversely affecting the tissues of wounds or surgical incisions.

The commercial porous PTFE sutures have a problem in that they do not have a sufficient tensile strength to satisfy the standards specified by the Ministry of Public Welfare of Japan in Notification No. 444.

SUMMARY OF THE INVENTION

The present invention has been achieved under these circumstances.

An object of present invention is to provide a surgical suture having predetermined tensile strength and elasticity and exhibiting good slipping property.

Another object of the present invention is to provide a process for producing a surgical suture having predetermined tensile strength and elasticity and exhibiting good slipping property.

Other objects and effects of the present invention will be apparent from the following description.

The present invention relates to a surgical suture comprising a porous body of polytetrafluoroethylene having an outer circumference that is substantially free of pores, with only the interior being made porous.

The present invention also relates to a process for producing a surgical suture which comprises the steps of: extruding a polytetrafluoroethylene paste to make an unsintered shape; stretching the unsintered shape at a temperature not higher than the melting point of the polytetrafluoroethylene to form a stretched shape; sintering the stretched shape; and drawing it into a filament through dies.

The present invention further relates to a process for producing a surgical suture which comprises the steps of: extruding a polytetrafluoroethylene paste to make an unsintered shape; stretching the unsintered shape at a temperature not higher than the melting point of the polytetrafluoroethylene; drawing the shape into a filament through dies at a temperature not higher than the melting point of the polytetrafluoroethylene; and sintering the filament.

BRIEF DESCRIPTION OF THE DRAWINGS

FIGS. 4A and 4B are a front view and a cross-sectional view, respectively, of a conventional monofilament suture;

FIGS. 5A and 5B are a front view and a cross-sectional view, respectively, of another conventional suture that is in the form of braided filaments;

FIGS. 6A and 6B are a front view and a cross-sectional view, respectively, of still another conventional suture that is in the form of twisted filaments.

DETAILED DESCRIPTION OF THE INVENTION

Figure 1:
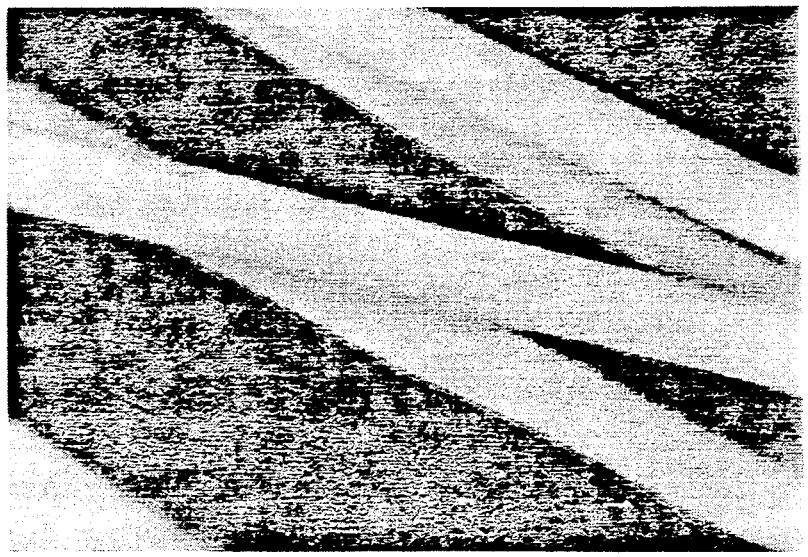
FIG. 1 is a scanning micrograph (magnification: 50) showing the outer surface of one of the sutures prepared in the example of the present invention.
Figure 2:
FIG. 2 is a scanning electron micrograph (magnification: 1,000) showing the outer surface of the same suture.
Figure 3:
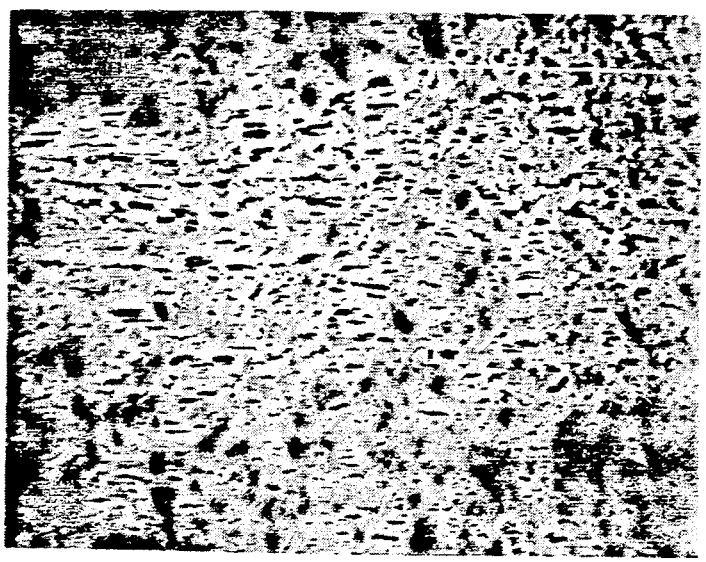
FIG. 3 is a scanning electron micrograph (magnification: 1,000) of the surface of the interior of the same suture.
Figure 7:
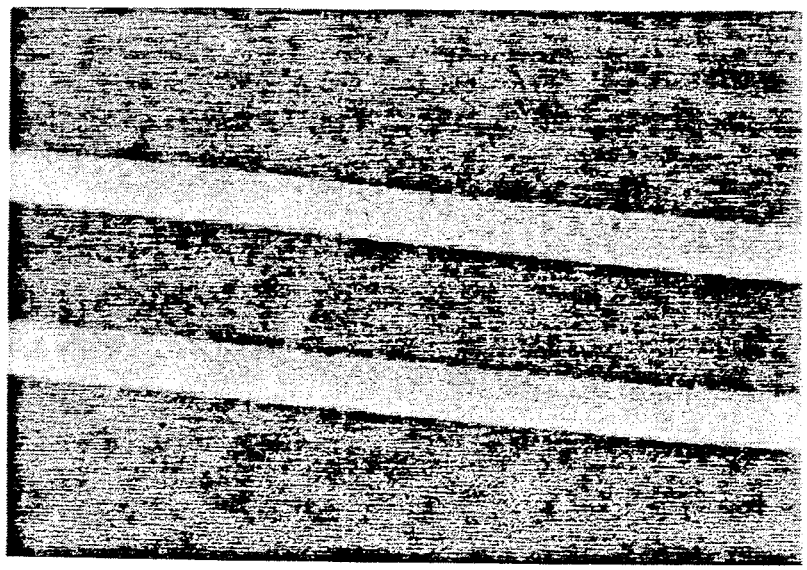
FIG. 7 is a scanning electron micrograph (magnification: 50) showing the outer surface of commercial porous PTFE sutures.

FIG. 1 shows the outer surface (circumference) of the suture of the present invention at a magnification of 50; FIG. 2 shows the outer surface (circumference) of the same suture at a higher magnification of 1,000; and FIG. 3 shows the inner surface of the same suture at a magnification of 1,000.

The surgical suture according to the present invention comprises a porous body of PTFE having an outer circumference that is substantially free of pores, with only the interior being made porous.

The thickness of the outer circumference substantially free of pores is not limited but is preferably such a thickness that does not deteriorate the properties of the porous body of PTFE such as elasticity.

The diameter of the suture of the present invention is not limited and any diameters used in this field of art can be applied.

The PTFE used in the present invention is generally a homopolymer composed of substantially only tetrafluoroethylene, and generally has a number average molecular weight of 500,000 or more, more preferably 5,000,000 or more. The PTFE is generally used in the form of fine powder as a starting material for the extrusion step.

In the process according to the present invention, methods for the extrusion, stretching and sintering steps, and the conditions therefor are not particularly limited, and may be those used in this field of art as described, e.g., JP-B-61-34346.

In the drawing step of the process according to the present invention, the drawdown ratio in the drawing operation through dies is preferably in the range of from 30 to 90%, and is more preferably in the range of from 60 to 90%, in total. The "drawdown ratio" as used herein is defined by the following formula:

$$\text{Drawdown ratio} = \frac{\text{Cross-sectional area of article before drawing}}{\text{Cross-sectional area of article after drawing}}$$

The drawing operation through dies is preferably conducted repeatedly, i.e., the drawing operation of a drawdown ratio of 80% or more, more preferably 90% or more, is preferably conducted repeatedly to obtain a predetermined total drawdown ratio. The drawing operation is preferably conducted at a temperature not higher than the melting point of the PTFE at a drawing speed of from 1 to 100 m/min.

The surgical suture of the present invention is porous and has a diameter slightly greater than the diameter of a needle so that its elasticity will prevent the leakage of blood through the eye of the needle.

In order to solve the problems associated with the prior art suture as described, e.g., in JP-B-61-34346, the suture of the present invention has the following characteristics: (i) it is made of a monofilament, and (ii) it has no pores in the outer surface (circumference), with only the interior being made porous. At the same time, in order to solve the problems with commercial porous PTFE sutures, the suture of the present invention is provided with increased tensile strength by reshaping through dies, while care should be taken to minimize the deterioration of the elastic characteristic of the suture that is necessary to prevent the leakage of blood through the eye of a needle.

The present invention is illustrated in more detail referring to the following example, but is not construed as being limited thereto.

EXAMPLE 1

1,000 g of PTFE fine powder ("CD-123", product of Asahi Fluoropolymer Co., Ltd.) was uniformly mixed with 280 g of a white oil as a liquid lubricant to make a paste. After preliminary shaping at a pressure of 50 kg/cm$^2$, the paste was fed into an extruder and shaped to rods having diameters 1.1 mm, 0.9 mm and 0.7 mm. The rods were submerged in trichloroethylene and the liquid lubricant was removed by extraction.

Subsequently, the rods were placed through a furnace (at ca. 250° C.) and stretched by 900% monoaxially in the longitudinal direction. While maintaining the stretched condition, the stretched rods were sintered by heating at ca. 500° C. for 1 minute. The sintered rods were drawn through successive dies in the following manner: the rod having a diameter of 1.1 mm as extruded was passed through dies with respective diameters of 0.30 and 0.27 mm; the rod having a diameter of 0.9 mm as extruded was passed through dies with respective diameters of 0.27, 0.25 and 0.23 mm; and the rod having a diameter of 0.7 mm as extruded was passed through dies with respective diameters of 0.25, 0.23 and 0.20 mm. As a result, sutures according to the present invention were obtained. The diameters before and after drawing are shown in Table 2 below.

TABLE 2

| | | | |
|---|---|---|---|
| Rod diameter (mm) | 1.1 | 0.9 | 0.7 |
| Diameter of sintered rod (mm) | 0.262 | 0.211 | 0.173 |
| Diameter after drawing (mm) | 0.235 | 0.180 | 0.138 |
| Drawdown ratio (%) | 80 | 73 | 64 |

$$\text{Drawdown ratio} = \frac{\text{Cross-sectional area of rod before passage through first die}}{\text{cross-sectional area of rod after passage through last die}}$$

The sutures thus produced were evaluated for their characteristics in accordance with the standards for plastic sutures specified by the Ministry of Public Welfare of Japan in Notification No. 444 (Extra Circular of Dec. 28, 1970). The results are shown in Table 3 below with corresponding standards in the Notification No. 444.

TABLE 3

| | | | |
|---|---|---|---|
| Diameter as extruded (mm) | 1.1 | 0.9 | 0.7 |
| Suture diameter (mm) | 0.235 | 0.180 | 0.138 |
| Tensile strength (kg) | 1.84 | 0.78 | 0.55 |
| Standards in Notification No. 444 | | | |
| Size code | 3-0 | 4-0 | 5-0 |
| Diameter (mm) | 0.203–0.254 | 0.152–0.203 | 0.102–0.152 |
| Tensile strength (kg) | ≧1.13 | ≧0.68 | ≧0.45 |

As the results in Table 3 show, the three suture samples prepared in accordance with the present invention satisfied the standard of the Ministry of Public Welfare of Japan.

These surgical sutures of the present invention were implanted in the body of rabbits and, after predetermined periods (1, 3 and 6 months), the sutures were extracted and evaluated for their tissue interaction. The tissue reaction evoked by the sutures of the present invention was obviously not as strong as that caused by the conventional tissues.

The suture of size code 4-0 of the present invention was examined with a scanning electron microscope (FIGS. 1, 2 and 3) and it was found to be substantially free of pores in the outer surface, with only the inner surface being porous.

FIG. 1 shows the outer surface of the sutures (magnification: 50); FIG. 2 shows showing the outer surface of the suture (magnification: 1,000); and FIG. 3 shows the surface of the interior of the suture (magnification: 1,000).

EXAMPLE 2

1,000 g of PTFE fine powder ("CD-123", product of Asahi Fluoropolymer Co., Ltd.) was uniformly mixed with 280 g of a white oil as a liquid lubricant to make a paste. After preliminary shaping at a pressure of 50 kg/cm$^2$, the paste was fed into an extruder and shaped to rods having diameters 1.1 mm, 0.9 mm and 0.7 mm.

The rods were submerged in trichloroethylene and the liquid lubricant was removed by extraction.

Subsequently, the rods were placed through a furnace (at ca. 250° C.) and stretched by 900% monoaxially in the longitudinal direction. The stretched rods were drawn through successive dies in the following manner: the rod having a diameter of 1.1 mm as extruded was passed through dies with respective diameters of 0.33 and 0.30 mm; the rod having a diameter of 0.9 mm as extruded was passed through dies with respective diameters of 0.30, 0.27 and 0.25 mm; and the rod having a diameter of 0.7 mm as extruded was passed through dies with respective diameters of 0.27, 0.25 and 0.23 mm. While maintaining the drawn state, the drawn articles were then sintered by heating at ca. 500° C. for 1 minute. As a result, sutures according to the present invention were obtained.

The sutures thus produced were evaluated for their characteristics in accordance with the standards for plastic sutures specified by the Ministry of Public Welfare of Japan in Notification No. 444 (Extra Circular of Dec. 28, 1970). The results are shown in Table 4 below with corresponding standards in the Notification No. 444.

TABLE 4

| | | | |
|---|---|---|---|
| Diameter as extruded (mm) | 1.1 | 0.9 | 0.7 |
| Suture diameter (mm) | 0.225 | 0.169 | 0.120 |
| Tensile strength (kg) | 1.83 | 0.81 | 0.51 |
| Standards in Notification No. 444 | | | |
| Size code | 3-0 | 4-0 | 5-0 |
| Diameter (mm) | 0.203–0.254 | 0.152–0.203 | 0.102–0.152 |
| Tensile strength (kg) | $\geq 1.13$ | $\geq 0.68$ | $\geq 0.45$ |

As the results in Table 4 show, the three suture samples prepared in accordance with the present invention satisfied the standard of the Ministry of Public Welfare of Japan.

The above-prepared sutures of the present invention was examined with a scanning electron microscope and it was found to be substantially free of pores in the outer surface, with only the inner surface being porous.

As described on the foregoing, the surgical sutures of the present invention has predetermined values of diameter, tensile strength and elasticity and exhibits a good slipping without adversely affecting the tissues of wounds or surgical incisions. A suture having such improved characteristics can be easily produced by the process of the present invention.

While the invention has been described in detail and with reference to specific examples thereof, it will be apparent to one skilled in the art that various changes and modifications can be made therein without departing from the spirit and scope thereof.

What is claimed is:

1. A surgical suture comprising a porous body of sintered polytetrafluoroethylene having an outer circumference that is substantially free of pores, with only the interior being made porous.

2. A surgical suture comprising a porous body of sintered polytetrafluoroethylene having an outer circumference that is substantially free of pores, with only the interior being made porous, being prepared by the steps of:
   extruding a polytetrafluoroethylene paste to make an unsintered shape;
   stretching said unsintered shape at a temperature not higher than the melting point of the polytetrafluoroethylene to form a stretched shape;
   sintering said stretched shape; and
   drawing the resultant sintered stretched shape into a filament through dies.

3. A surgical suture comprising a porous body of sintered polytetrafluoroethylene having an outer circumference that is substantially free of pores, with only the interior being made porous, being prepared by the steps of:
   extruding a polytetrafluoroethylene paste to make an unsintered shape;
   stretching said unsintered shape at a temperature not higher than the melting point of the polytetrafluoroethylene;
   drawing the shape into a filament through dies at a temperature not higher than the melting point of the polytetrafluoroethylene; and
   sintering said filament.

* * * * *

UNITED STATES PATENT AND TRADEMARK OFFICE
CERTIFICATE OF CORRECTION

PATENT NO. : 5,258,014
DATED : November 2, 1993
INVENTOR(S) : Harada et al

It is certified that error appears in the above-indentified patent and that said Letters Patent is hereby corrected as shown below:

Delete Column 3, between lines 17-21, and insert therefor as follows:

-- $$\text{Drawdown ratio} = \frac{\text{Cross-sectional area of article after drawing}}{\text{Cross-sectional area of article before drawing}}$$ --

Delete Column 4, between lines 16-20, and insert therefor as follows:

-- $$\text{Drawdown ratio} = \frac{\text{Cross-sectional area of rod after passage through last die}}{\text{Cross-sectional area of rod before passage through first die}}$$ --

Signed and Sealed this

Twenty-seventh Day of September, 1994

Attest:

BRUCE LEHMAN

*Attesting Officer*      *Commissioner of Patents and Trademarks*